(12) United States Patent
Adams et al.

(10) Patent No.: US 10,433,851 B2
(45) Date of Patent: Oct. 8, 2019

(54) BRAIDED VASCULAR DEVICES HAVING NO END CLAMPS

(71) Applicant: St. Jude Medical, Cardiology Division, Inc., St. Paul, MN (US)

(72) Inventors: Daniel O. Adams, Long Lake, MN (US); Paul Pignato, Stacy, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 195 days.

(21) Appl. No.: 15/231,258

(22) Filed: Aug. 8, 2016

(65) Prior Publication Data

US 2016/0345979 A1     Dec. 1, 2016

Related U.S. Application Data (63) Continuation of application No. 11/861,954, filed on Sep. 26, 2007.

(51) Int. Cl.
*A61B 17/12* (2006.01)
*A61B 17/00* (2006.01)

(52) U.S. Cl.
CPC .... *A61B 17/12109* (2013.01); *A61B 17/0057* (2013.01); *A61B 17/12022* (2013.01);
(Continued)

(58) Field of Classification Search
CPC .. A61F 2/064; A61F 2/848; A61F 2220/0008; A61F 2002/821–91591; A61F 2230/0082; A61F 2230/0084; A61F 2230/008; A61F 2230/0078; A61F 2250/0039; A61F 2002/068; A61B 2017/00575; A61B 2017/00606; A61B 17/0057; A61B 17/12022; A61B 17/12036; A61B 17/12027; A61B 17/12031;
(Continued)

(56) References Cited

U.S. PATENT DOCUMENTS 3,874,388 A    4/1975 King et al.
4,007,743 A    2/1977 Blake
(Continued)

FOREIGN PATENT DOCUMENTS

EP    0541063 A2    5/1993
SU    1468511 A1    3/1989
WO    93/10714 A1    6/1993

OTHER PUBLICATIONS

Diab, Ka, Cao, Q. L., and Hijazi, Z. M., "Percutaneous Device Closure of Congenital VSDs", Cardiac Interventions Today, Jun. 2007, pp. 23-27 with cover page.
(Continued)

*Primary Examiner* — Christopher L Templeton
(74) *Attorney, Agent, or Firm* — Armstrong Teasdale LLP (57) ABSTRACT

In some embodiments, a medical device may include one or more of the following features: (a) a metal fabric formed of braided metal strands, (b) the medical device having a collapsed configuration for delivery through a channel in a patient's body and having a generally dumbbell-shaped expanded configuration with two expanded diameter portions, separated by a reduced diameter portion formed between opposed ends of the device and unsecured metal strand ends at the opposed ends, and (d) a thrombogenic agent located on the metal fabric.

18 Claims, 5 Drawing Sheets

(52) U.S. Cl.
CPC .. *A61B 17/12036* (2013.01); *A61B 17/12113* (2013.01); *A61B 17/12172* (2013.01); *A61B 17/12177* (2013.01); *A61B 2017/00575* (2013.01); *A61B 2017/00615* (2013.01); *A61B 2017/00623* (2013.01); *A61B 2017/00867* (2013.01); *A61B 2017/12054* (2013.01); *A61B 2017/12095* (2013.01)

(58) Field of Classification Search
CPC ........ A61B 17/12099; A61B 17/12104; A61B 17/12109; A61B 17/12122; A61B 17/12113; A61B 17/12172; A61B 17/12131; A61B 17/12168
See application file for complete search history.

(56) References Cited

U.S. PATENT DOCUMENTS

| | | | |
|---|---|---|---|
| 4,619,246 A | 10/1986 | Molgaard-Nielsen et al. | |
| 4,836,204 A | 6/1989 | Landymore et al. | |
| 4,917,089 A | 4/1990 | Sideris | |
| 4,921,484 A | 5/1990 | Hillstead | |
| 4,991,602 A | 2/1991 | Amplatz et al. | |
| 5,026,377 A | 6/1991 | Burton et al. | |
| 5,061,275 A | 10/1991 | Wallsten et al. | |
| 5,064,435 A | 11/1991 | Porter | |
| 5,067,489 A | 11/1991 | Lind | |
| 5,108,420 A | 4/1992 | Marks | |
| 5,171,259 A | 12/1992 | Inoue | |
| 5,334,217 A | 8/1994 | Das | |
| 5,451,235 A | 9/1995 | Lock et al. | |
| 5,456,693 A | 10/1995 | Conston et al. | |
| 5,466,242 A | 11/1995 | Mori | |
| 5,522,822 A | 6/1996 | Phelps et al. | |
| 5,545,208 A | 8/1996 | Wolff et al. | |
| 5,575,818 A | 11/1996 | Pinchuk | |
| 5,618,301 A * | 4/1997 | Hauenstein ............... | A61F 2/06 606/198 |
| 5,667,486 A | 9/1997 | Mikulich et al. | |
| 5,683,411 A | 11/1997 | Kavteladze et al. | |
| 5,725,552 A | 3/1998 | Kotula et al. | |
| 5,741,333 A | 4/1998 | Frid | |
| 5,755,772 A | 5/1998 | Evans et al. | |
| 5,846,261 A | 12/1998 | Kotula et al. | |
| 5,941,895 A * | 8/1999 | Myler ................... | A61M 29/00 606/195 |
| 6,096,052 A | 8/2000 | Callister et al. | |
| 6,123,715 A | 9/2000 | Amplatz | |
| 6,168,622 B1 | 1/2001 | Mazzocchi | |
| 6,217,609 B1 | 4/2001 | Haverkost | |
| 6,355,057 B1 * | 3/2002 | DeMarais ................. | A61F 2/91 623/1.15 |
| 6,432,116 B1 | 8/2002 | Callister et al. | |
| 6,451,048 B1 | 9/2002 | Berg et al. | |
| 6,468,303 B1 | 10/2002 | Amplatz et al. | |
| 6,562,066 B1 | 5/2003 | Martin | |
| 6,638,257 B2 | 10/2003 | Amplatz | |
| 7,108,716 B2 | 9/2006 | Burnside et al. | |
| 7,306,624 B2 | 12/2007 | Yodfat et al. | |
| 7,445,623 B2 | 11/2008 | Mialhe | |
| 2002/0029051 A1 | 3/2002 | Callister et al. | |
| 2003/0083734 A1 | 5/2003 | Friedrich et al. | |
| 2003/0153935 A1 | 8/2003 | Mialhe | |
| 2004/0088037 A1 * | 5/2004 | Nachreiner ............... | A61F 2/90 623/1.15 |
| 2006/0100684 A1 | 5/2006 | Elliott | |
| 2006/0224183 A1 | 10/2006 | Freudenthal | |
| 2006/0241690 A1 | 10/2006 | Amplatz et al. | |
| 2006/0253184 A1 | 11/2006 | Amplatz | |
| 2007/0043391 A1 | 2/2007 | Moszner et al. | |
| 2007/0118207 A1 | 5/2007 | Amplatz et al. | |
| 2007/0150041 A1 | 6/2007 | Evans et al. | |
| 2007/0167980 A1 | 7/2007 | Figulla et al. | |
| 2007/0179590 A1 * | 8/2007 | Lu ............................. | A61F 2/07 623/1.16 |
| 2008/0051830 A1 | 2/2008 | Eidenschink et al. | |
| 2008/0228256 A1 | 9/2008 | Erickson et al. | |
| 2008/0262518 A1 | 10/2008 | Freudenthal | |
| 2010/0094409 A1 * | 4/2010 | Barker ...................... | A61F 2/07 623/1.46 |

OTHER PUBLICATIONS

Yong, G., Salinger, M. H., and Feldman, T. E., "Device Close for PFO", Cardiac Interventions Today, Jun. 2007 pp. 32-39.
Zajarias, A., and Lasala, J. M., "Percutaneous Management of Atrial Septal Defects", Cardiac Interventions Today, Jun. 2007, pp. 45-49.

* cited by examiner

(PRIOR ART)

*Fig. 1A*

(PRIOR ART)

*Fig. 1B*

(PRIOR ART)

*Fig. 1C*

(PRIOR ART)

*Fig. 2*

(PRIOR ART)

BRAIDED VASCULAR DEVICES HAVING NO END CLAMPS

CROSS-REFERENCE TO RELATED APPLICATIONS

This application is a continuation application of U.S. patent application Ser. No. 11/861,954, filed on Sep. 26, 2007, the entire contents and disclosure of which are hereby incorporated herein by reference in their entirety.

FIELD OF THE INVENTION

Embodiments of the present invention generally relate to intravascular devices for treating medical conditions. Particularly, embodiments of the present invention relate to intravascular devices for treating vascular conditions. More particularly, embodiments of the present invention relate to intravascular devices for selective occlusion of a vessel and/or shunting or restricting flow in a vessel or organ within the body's circulatory system.

BACKGROUND

A wide variety of intravascular devices are used in various medical procedures. Certain intravascular devices, such as balloon catheters, diagnostic catheters, stent delivery catheters, and guidewires are generally used simply to deliver fluids or other medical devices to specific locations within a patient's body, such as a selective site within the vascular system. Other, frequently more complex, devices are used in treating specific conditions, such as devices used in removing vascular occlusions or for treating septal defects and the like.

In certain circumstances, it may be necessary to occlude a patient's vessel, chamber, channel, hole, or cavity such as to stop blood flow there through. In other cases it may be necessary to create a flow restriction or to shunt flow from one vessel to another to treat abnormal cardiovascular conditions. Examples of selective occlusion are, without limitation, closure of a Patent Ductus Arteriosus (PDA), Atrial Septal Defect (ASD), Ventricular Septal Defect (VSD), Patent Foreman Ovale (PFO), Arterial Venous Fistula (AVF), or an Arterial Venous Malformation (AVM).

Mechanical embolization devices are well known in the art and sold commercially for occlusion of vessels in various locations within the vasculature. Intravascular occlusion devices can be fabricated from Nitinol (NiTi) wire strands that have been braided to form a tubular fabric which is then heat set in a mold to an expanded shape, but which can be compressed for delivery through a catheter to a treatment site whereby the device, when urged out of the delivery catheter, self-expands within the vasculature to occlude blood flow at the treatment site. The details of the various designs and configurations as well as methods of fabricating and using the devices are known in the art.

An example of a shunting procedure is shunting of blood between the portal vein and the hepatic vein; know as a Transjugular Intrahepatic Portosystemic Shunt (TIPS). Certain forms of congenital disease may require a communication between the right atrium and left atrium. Shunting may also be required for treating specific abnormal conditions, such as bi-passing vascular occlusions within an internal passageway.

Congenital heart defects are examples of the necessity for flow restriction where holes in the septum allow blood to flow from the high pressure left ventricle to the lower pressure right ventricle causing excess blood flow to the lungs. The body's natural reaction is to constrict the vessels to the lungs to restrict blood flow. Over time, this causes a thickening of the pulmonary arteries and ultimately leads to closure of smaller lung arteries and further complications if left untreated. The treatment involves early mechanical flow restriction of blood to the lungs until a surgical fix can be accomplished.

The occluding, shunting, and flow restricting devices described above use similar technology for fabrication. Each device is formed from a plurality of resilient metal strands of a shape memory alloy woven into a braided fabric to create a resilient material which can be heat treated to substantially set a desired shape. In performing the heat treatment step, the braided fabric is first deformed to generally conform to a molding surface of a molding element and the braided fabric is then heat treated in contact with the surface of the molding element at an elevated temperature. The time and temperature of the heat treatment is selected to substantially set the braided fabric in its deformed state. After the heat treatment, the fabric is removed from contact with the molding element and will substantially retain its shape in the deformed state. The braided fabric so treated defines an expanded state of a medical device, but which can be longitudinally stretched to reduce its cross-sectional profile so that it can be deployed through a catheter into a channel in a patient's body. The device connects to a delivery device by a threaded connection. Once the delivery catheter's distal end with the device contained within its lumen is placed at the treatment site, the device is urged out of the delivery catheter and self-expands to its expanded preset configuration. Once the device is positioned as desired, the delivery device is unthreaded and the delivery catheter and delivery device are removed from the body.

One limitation of these devices is the need to clamp the ends of the wire strands at each end of the device to prevent unraveling. In such untreated NiTi fabrics, the strands will tend to return to their unbraided configuration and the braid can unravel fairly quickly unless the ends of the length of braid that has been cut to form the device, are constrained relative to one another. One method which has proven to be useful to prevent the braid from unraveling is to clamp the braid at two locations and cut the braid to leave a length of the braid having clamps at either end, thereby effectively defining an empty space within a sealed length of fabric. These clamps will hold the ends of the cut braid together and prevent the braid from unraveling.

Alternatively, one can solder, braze, weld or otherwise affix the ends of the desired length together (e.g., with a biocompatible cementitious organic material) before cutting the braid. Although soldering and brazing of NiTi alloys have proven to be fairly difficult, the ends can be welded together, such as by spot welding with a laser welder.

Devices marketed using these technologies include the braided metal clamps to prevent unraveling of the metal strands. The clamps add to the diameter of the collapsed device for delivery through a catheter as well as project outward from some configurations of the device. These outward projections are often in the blood flow path and could be a source of clot formation or result in flow disruption.

Some have provided a recess in each end surface of the device where each braided end of the device is held together with a clamp. The clamps are recessed into the expanded diameter portion of the device, thereby reducing the overall length dimension of the device and creating a low profile occluder. However, the recessed clamps cause the fabric to reverse direction in the heat-set state. In the compressed state, the wires are higher stressed and exert an increased outward drag against the wall of the delivery catheter making it more difficult to push the device through the catheter.

In the case of a flow restrictor or shunt device, the braided wire end clamps make the device configuration bulky and un-necessarily complex, since the natural placement of the clamps is in a co-axial position to the braided tube, which ideally, is where the flow path should be. The designs described require extra manufacturing steps to create the flow path. In addition the manufacturing cost of the device is higher than need be if the clamps were not used.

Figure 1A:
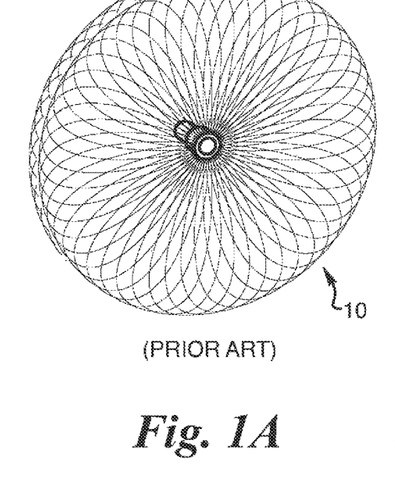
FIG. 1A shows a perspective view of a prior art occluder.
Figure 1B:
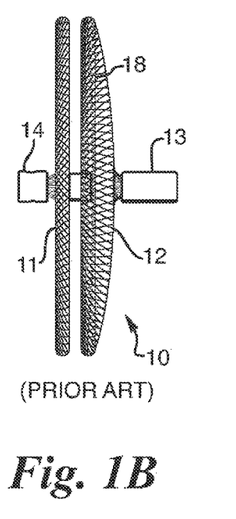
FIG. 1B shows a side view of the occluder design of FIG. 1A.
Figure 1C:
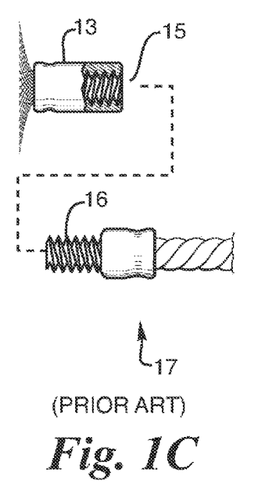
FIG. 1C shows an enlarged view of a clamp used in the occluder of FIG. 1A along with a delivery device threaded end.
Figure 2:
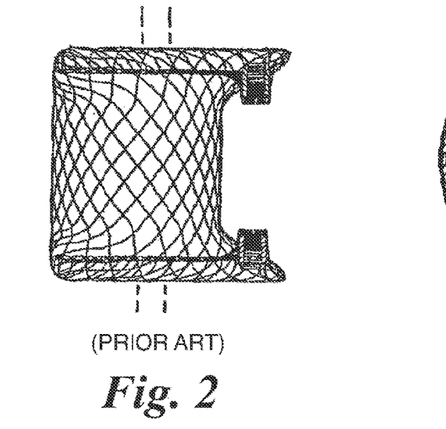
FIG. 2 shows a side view of a prior art shunt device having an eccentric lumen and two discs with recessed securement connectors.
Figure 3:
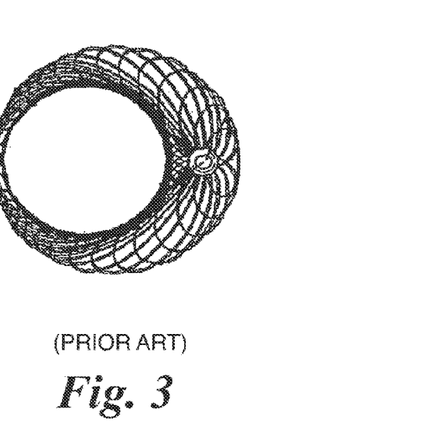
FIG. 3 shows a top view of a shunt device of FIG. 2 having an eccentric lumen and two discs with recessed securement connectors.
Figure 4:
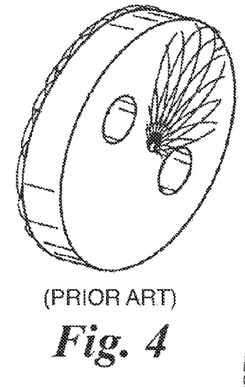
FIG. 4 shows a perspective view of a prior art flow restrictor.

With reference to FIGS. 1A-C, 2, 3, and 4, prior occluders, shunts, and flow restrictors are shown respectively. FIGS. 1A-C illustrate an occluder design that may be described as having a flanged or disc shape at each end, connected by a smaller diameter portion between them. FIGS. 2 & 3 are two views of a shunt device. FIG. 4 is an example of a flow restrictor.

FIG. 1A shows the design of an occluder 10 having enlarged diameter discs or flanges 11 & 12 at each end and a small connecting diameter between the ends. Each end of the device has a wire end clamp. The distal clamp 14 and proximal clamp 13 hold the wire ends from unraveling. The side view FIG. 1B illustrates how clamps 13 extend from the end of the device. Clamp 13 contains internal threads 15 that mate with external threads 16 on delivery device 17 as depicted in FIG. 1C. A polyester fabric disc 18 is used to improve device thrombogenicity and is sutured into disc 12. The fabric collapses with the device for delivery through a delivery catheter.

It would be desirable for a medical device to achieve occlusion, flow restriction, or shunting of blood in the human vasculature that is:
of a lower collapsed deliverable profile;
deliverable through a delivery catheter with less force;
less intensive to manufacture;
less disruptive to blood flow; and
can be manufactured at a reduced cost.

SUMMARY OF THE INVENTION

In some embodiments, a collapsible medical device may include one or more of the following features: (a) at least one layer of a plurality of metal strands woven into a tubular braided metal fabric having a proximal end, a distal end, and a segment there between, (b) the tubular woven metal fabric having an expanded preset configuration shaped for treatment of an opening in a body organ, (c) the expanded preset configuration being deformable to a lesser cross-sectional dimension for delivery through a channel in a patient's body, the woven metal fabric having a memory property whereby the medical device returns to the expanded preset configuration when delivered into the patient's body, said proximal and distal ends being free of clamps and having at least a portion of the segment larger in diameter than the free wire ends in the expanded preset configuration, and (d) an occluding fiber retained within an expandable hollow central portion formed by said tubular woven fabric.

In some embodiments, a medical device may include one or more of the following features: (a) a metal fabric formed of braided metal strands, (b) the medical device having a collapsed configuration for delivery through a channel in a patient's body and having a generally dumbbell-shaped expanded configuration with two expanded diameter portions separated by a reduced diameter portion formed between opposed ends of the device and unsecured metal strand ends at the opposed ends, and (d) a thrombogenic agent located on the metal fabric.

In some embodiments, a method of forming a medical device may include one or more of the following steps: (a) providing a metal fabric formed of a plurality of braided strands, the strands being formed of a metal which can be heat treated to substantially set a desired shape, (b) deforming the metal fabric to generally conform to a wall surface of a moulding element, (c) heat treating the metal fabric in contact with the surface of the moulding element at an elevated temperature, the temperature and the duration of the heat treatment being sufficient to substantially set the shape of the fabric in its deformed state, (d) removing the metal fabric from contact with the moulding element, (e) cutting the fabric adjacent the device side of the clamps after heat treatment, (f) clamping the opposite ends of the strands before deforming the metal fabric, (g) cutting an appropriately sized piece of the metal fabric, and (h) forming a long tubular braid from the metal fabric.

In some embodiments, a method for delivering a self-expanding medical device to a selected site in a vascular system may include one or more of the following steps: (a) selecting the combination of: (i) a delivery device inner catheter having a lumen extending from a proximal end to a distal end, the delivery device having an outer diameter adapted to slidingly fit within the lumen of a delivery catheter, (ii) an elongate, flexible member coaxially insertable through the lumen of the delivery device catheter, said elongate flexible member having a plunger member affixed thereto sized to at least partially fit within the lumen of the delivery device catheter when a proximally directed tension force is applied to the elongate flexible member with respect to the delivery device catheter, (iii) a braided tubular device with free ends of individual strands comprising the device captured between the plunger member and the delivery device catheter, (b) feeding the delivery device catheter with the braided tubular device attached through a lumen of the delivery catheter and out thereof, (c) moving the elongate flexible member relative to the tubular delivery device catheter to release the tubular device from the tubular delivery device catheter, (d) releasing a plunger spring located in the plunger member to capture the free ends between the plunger member and the inner delivery device catheter, (e) inserting the delivery catheter within a patient's vasculature, (f) repositioning the braided tubular device if it is not positioned properly upon release from the tubular delivery device catheter, (g) removing the delivery device from the patient's vasculature, (h) removing the delivery catheter from the patient's vasculature.

DESCRIPTION OF THE PREFERRED EMBODIMENT

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings. It's understood that the embodiments of the present teachings can be applied to occluders, shunts, or flow restrictors.

Embodiments of the present invention can be well suited for the selective occlusion, shunting, or flow restriction of a vessel, lumen, channel, cavity, or organ within the body's circulatory system. Embodiments of the present invention disclose a vascular occlusion, flow restriction, or shunt device formed of a plurality of wire strands woven into a braided tubular metal fabric having an expanded preset configuration and an elongated collapsed reduced diameter configuration. The device can be delivered through a catheter to a treatment site and shaped to create an occlusion, flow restriction, or shunt, when placed in an opening in a body organ or vessel. The woven metal fabric can have a memory property whereby the medical device tends to return to an expanded preset configuration when unconstrained. The device can have proximal and distal unsecured wire ends and a segment there between the wire ends having at least a portion of the segment larger in diameter than the unsecured wire ends in the expanded preset configuration.

Embodiments of the present invention can be fabricated from many various methods including those described in U.S. Pat. No. 6,123,715, titled Method of forming medical devices; intravascular occlusion devices, to Amplatz herein incorporated by reference in its entirety. Additionally, while it could be helpful to temporarily clamp or otherwise fix the wire ends during the wire cutting operation and during heat treatment to set the desired device shape, the inventors have discovered that the clamps are not needed after the heat treatment process since the heat treatment imparts a wire shape memory that resists unraveling of the braid wire ends. The elimination of the clamps reduces the device profile by elimination of the material of the clamps which surrounded the wires. In addition the wire ends may be positioned in an end wall of the device and need not be oriented outward from the device in an axial orientation as in prior devices. The recessing of the device end surfaces to hide the clamps is not required since the wire ends can be incorporated into the plane of the end surfaces of the device which simplifies the fabrication process and reduces manufacturing cost. Since the recessing of the device end surfaces is not required, the fabric reverse bends near the clamp are not required and the delivery forces are reduced during passage through the delivery catheter.

In the case of shunt devices or a flow restrictor such fabrication methods can be used such as those described in U.S. Pat. No. 6,468,303, titled "Retrievable Self Expanding Shunt", by Amplatz et al. and U.S. Pat. No. 6,638,257, titled "Intravascular Flow Restrictor", by Amplatz et. al. herein incorporated by reference in their entirety. In shunts and flow restrictors the elimination of the wire end clamps allow the axial area of the device ends to be available as a flow passage, simplifying the device design and lowering the device profile and manufacturing cost.

In the prior art solutions described herein, at least one of the wire end clamps served as a means to connect a delivery device. This was accomplished by providing internal (female) threads in at least one clamp that mated with external (male) threads on the delivery device. However, embodiments of the present invention disclose that the clamps are no longer necessary and therefore a new delivery system is disclosed below in more detail. The new delivery system includes an outer tubular guide catheter, an inner tubular delivery (pusher) catheter coaxially disposed and slidable relative to the outer guide catheter. An elongated flexible guide wire or cable that is coaxially insertable through the lumen of the inner tubular catheter that has a frusto-conical bead affixed at the distal end thereof sized to at least partially fit within the lumen of the inner pusher catheter when a proximally directed tension force is applied between the elongated flexible wire or cable with respect to the pusher catheter. By inserting a compressed coiled spring between a proximal end portion of the cable, the requisite clamping force is maintained to secure the device proximal wire ends to the distal end of the pusher catheter until the compression spring force is removed. Such a delivery system and improvements there to are described by Pending Patent Application U.S. Patent Publication No. 2006/0253184, titled "System for the Controlled Delivery of Stents and Grafts", by Amplatz et al. and by U.S. Patent Publication No. 2007/0118207, titled "System for Controlled Delivery of Stents and Grafts", by Amplatz et al, herein incorporated by reference in its entirety.

In one embodiment of the invention, a simplified medical device and a method of fabrication of a medical device, without the limitations inherent to having wire end clamps, for treating vascular or organ abnormalities which necessitate occlusion, flow restriction or shunting as the method of treatment is disclosed. In another embodiment of the present invention, a method of treating a medical condition requiring the occlusion, flow restriction, or shunting of blood flow in a vessel or cavity within the body's vasculature using a simplified medical device fabricated from a resilient braided metal fabric having a preset expanded configuration and a collapsed configuration for delivery through the vasculature using a novel delivery system is disclosed.

These and other features and advantages of the inventive design will become readily apparent to those skilled in the art from a review of the drawings and the detailed description of the preferred embodiment in conjunction with the accompanying claims and drawings.

Figure 5A:
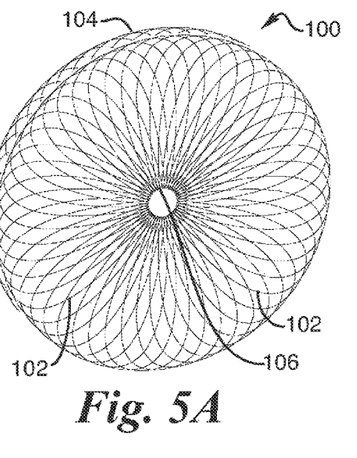
FIG. 5A shows a perspective view of an occluder without end clamps in an embodiment of the present invention.
Figure 5B:
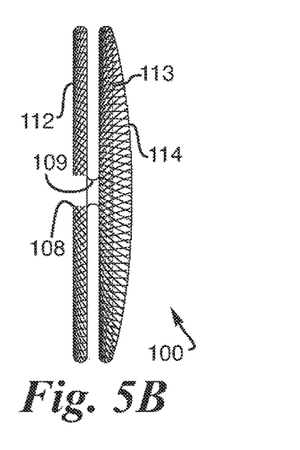
FIG. 5B shows a side view of an occuluder without end clamps in an embodiment of the present invention.

With reference to FIG. 5A-B, perspective views of an occluder without end clamps is shown. Embodiments of the present invention disclose an occluder 100 that can be formed of a plurality of wire strands 102 woven into a braided metal fabric 104 having an expanded preset configuration as shown by discs 112 and 114 and an elongated collapsed reduced diameter configuration 115 for delivery through a catheter sleeve 120 to a treatment site (FIG. 5). The device can also be shaped to create a flow restrictor or shunt when placed in an opening in a body organ or vessel as discussed above in detail. Woven metal fabric 104 can have a memory property whereby occluder 100 tends to return to an expanded preset configuration when unconstrained (e.g., by catheter sleeve 120). Occluder 100 can have proximal and distal unsecured wire ends 106 and 108 and a segment 109 there between, having at least a portion of the segment larger in diameter than the unsecured wire ends in the expanded preset configuration.

Metal strands 102 define two sets of essentially parallel generally helical strands, with the strands of one set having a "hand" (e.g., a direction of rotation, opposite that of the other set). This is a generally tubular fabric 104, known in the fabric industry as a tubular braid. The pitch of wire strands 102 (e.g., the angle defined between the turns of the wire and the axis of the braid) and the pick of fabric 104 (e.g. the number of wire crossovers per unit length) may be adjusted as desired for a particular application. Wire strands 102 of metal fabric 104 used can be formed of a material which is both resilient and which can be heat treated to substantially set a desired shape. Materials which are suitable for this purpose include a cobalt-based low thermal expansion alloy referred to in the field as Elgeloy, nickel-based high temperature-high-strength "superalloys" commercially available from Haynes International located in Kokomo, Ind. under the trade name Hastelloy, nickel-based heat treatable alloys sold under the name Incoloy by International Nickel located in Toronto, Canada, and a number of different grades of stainless steel. A factor in choosing a suitable material for wires 102 is that they retain a suitable amount of the deformation induced by the molding surface when subjected to a predetermined heat treatment.

One class of materials which meet these qualifications are so-called shape memory alloys. One particularly preferred shape memory alloy for use in the present method is a Nitinol alloy that is very elastic—this alloy is said to be "superelastic" or "pseudoelastic". This elasticity will help a device return to a preset expanded configuration for deployment.

Figure 6:
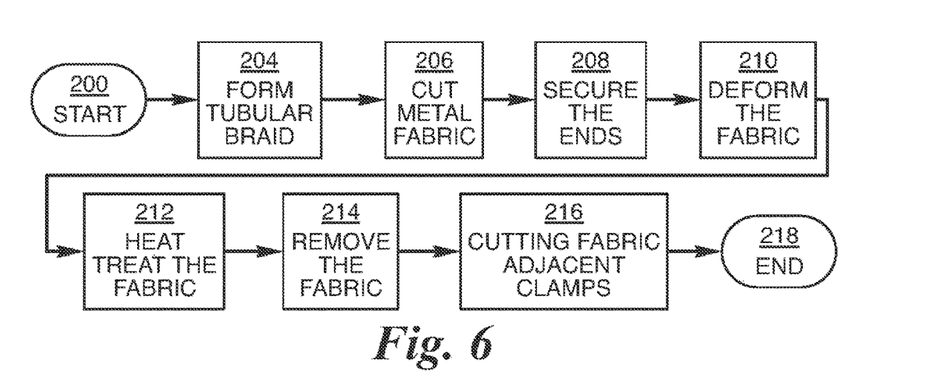
FIG. 6 shows a flowchart diagram of a method of manufacturing a medical device in accordance with embodiments of the present invention.

With reference to FIG. 6, a flowchart diagram of a method of manufacturing a medical device in accordance with embodiments of the present invention is shown. Manufacturing process 200 begins at state 204 where a large piece of fabric 104 which is formed, for example, by braiding wire strands 102 to form a long tubular braid. At state 206, ends 106 and 108 can be secured. One can clamp, tape, solder, braze, weld or otherwise affix ends 106 and 108 to the desired length (e.g., length greater than final device length) together (e.g., with a biocompatible cementitious organic material) before cutting the braid. At state 208, an appropriately sized piece of metal fabric 104 is cut from the larger piece of fabric 104 by cutting outside the clamps, leaving the clamps to contain the braid ends of the device segment, Metal sleeves clamped or swaged onto the braid are a preferred clamp design and can be easily removed after heat treatment by cutting the fabric adjacent the clamps. Since the clamps contain braided heat set filaments set in the axial direction, the braid should be cut to place the wire ends in the plane of the device ends. Compressing the heat set shape or elongating the braid by pulling on the clamps allows the braid to be placed into a small diameter sleeve for holding purposes during the braid cutting process. A laser or mechanical cutter as well known in the art may be used to cut the braid. Mechanical cutting may require deburring of sharp wire cut ends.

Using a temporary clamp is helpful as it can be removed easily after heat treatment. Permanent wire end bonds would need to be cut off after heat treatment. Tape can also hold the ends from unraveling during handling but will not survive the heat treatment; however, at this point in the process minor unraveling is not a factor since the final device braided fabric length will be shortened by cutting.

Once an appropriately sized piece of metal fabric 104 is obtained, fabric 104 is deformed at state 210 to generally conform to a surface of a molding element. Deforming the fabric will re-orient the relative positions of the strands of the metal fabric from their initial order to a second, re-oriented configuration. The shape of the molding element should be selected to deform the fabric into substantially the expanded shape of the desired component of the medical device.

Once the molding element is assembled with metal fabric 104 generally conforming to a molding surface of that element, fabric 104 can be subjected to a heat treatment at state 212 while it remains in contact with that molding surface. Suitable heat treatments of Nitinol wire to set a desired shape are well known in the art. It has been found that holding a Nitinol fabric at about 500° C. to about 550° C. for a period of about 1-30 minutes, depending on the softness or harness of the device to be made, will tend to set fabric 104 in its deformed state, e.g. (wherein it conforms to the molding surface of the molding element). At lower temperatures the heat treatment time will tend to be greater (e.g., about one hour at about 350° C.) and at higher temperatures the time will tend to be shorter (e.g., about 30 seconds at about 900 degrees C.). After the heat treatment and cooling, fabric 104 is removed from contact with the molding element at state 214 and will substantially retain the molded shape.

At step 216, the fabric adjacent the device side of the clamps is cut after heat treatment. Thus cutting the fabric adjacent the clamps inherently removes the clamps. Any temporary wire clamps or other means of holding the wire ends, if used, are thus removed at state 216 after the heat treatment process by cutting the braided wire adjacent the clamps as previously explained, to provide a desired final device length at state 218.

Figure 5C:
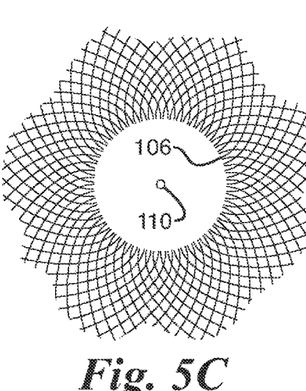
FIG. 5C shows an enlarged wire end view of an occluder without end clamps.

With reference again to FIGS. 5A-C an occluder without end clamps is shown. It is noted there are no clamps for wire ends 106 and 108. Discs 112 and 114, after heat treatment and removal from the mold, can be axially elongated by compressing them such that occluder 100 elongates and can be advanced into a cut to length fixture. The excess length from each end can be trimmed by manually cutting or using a laser to cut wires 102 to length. As illustrated in FIG. 5B, the cut length can be such that wire ends 106 and 108 are positioned near device central axis 110. Alternatively, wire ends 106 and 108 could be cut shorter resulting in wire ends 106 and 108 positioned into a larger diameter. The result is occluder 100 is shorter in length compared to know prior art devices and there are no clamps. As is known in the art, a polyester fabric disc 113 can be used to improve device thrombogenicity and can be sutured into disc 114. For an occluder device the fabric disk 114 could have no central passage as opposed to the case for a flow restrictor or shunt device where a central flow passage in fabric disk 114 if used could be fabricated to allow for controlled blood passage.

Figure 5D:
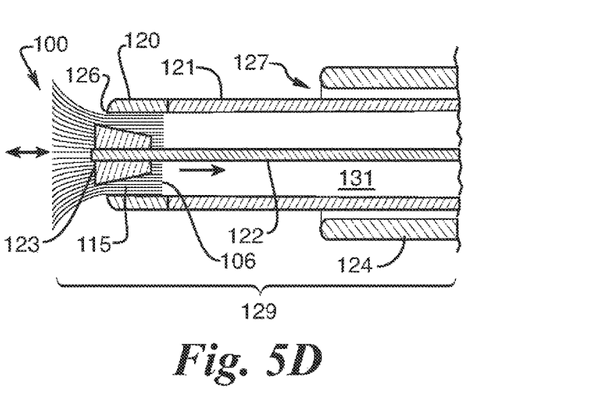
FIG. 5D shows a delivery device in an embodiment of the present invention.

FIG. 5D shows wire ends 106 pushed into a delivery catheter sleeve 120. Delivery system 129 includes an outer tubular guide catheter 124, an inner tubular delivery (pusher) catheter 121 coaxially disposed and slidable relative to outer guide catheter 124. The delivery system comprises an elongated flexible guide wire 122 or cable that is coaxially insertable through lumen 131 of the inner tubular catheter 121 and that has a frusto-conical bead 123 affixed at the distal end thereof sized to at least partially fit within lumen 131 of the inner pusher catheter 121 when a proximally directed tension force is applied between the elongated flexible wire or cable with respect to pusher catheter 121. By inserting a compressed coiled spring between a proximal end portion of cable 122 and a fixed hub on pusher catheter 121, the requisite clamping force is maintained to secure occluder 100 proximal wire ends 106 to the distal end of pusher catheter 121 until the compression spring force is removed. A frusto-conical plunger 123 moves axially with the shaft 122 to clamp the inside of wire ends 106 or 108 against the inside surface of sleeve 120. Sleeve 120 is attached to the distal end of pusher catheter 121. Plunger 123 is spring loaded to clamp device wire ends 106 or 108 but can be released by advancement of shaft 122 to release occluder 100 when properly positioned in a body. With ends 106 or 108 clamped within sleeve 120, occluder 100 may be drawn proximally into a delivery catheter 124 coaxially arranged over pusher catheter 121. Once delivery catheter 124 is advanced within the vasculature adjacent the site of treatment, the delivery device may be advanced or catheter 124 withdrawn to allow occluder 100 to freely self expand to its pre-determined memorized shape. Once occluder 100 is in place, occluder 100 is released by advancing frustoconical clamping mechanism 123 relative to sleeve 120. With occluder 100 fully deployed the delivery system 129 is removed from the body, leaving occluder 100 implanted at the treatment site.

In the embodiment shown in FIG. 1A-C, polyester fabric 18 provides an occluding surface across device 10 and therefore the choice of location for cutting the wire ends is not that critical. Wire ends 106 could be cut and lie anywhere in outer discs 112 and 114 but preferably are near central axis 110 to provide a double wall to discs 112 and 114.

Figure 7A:
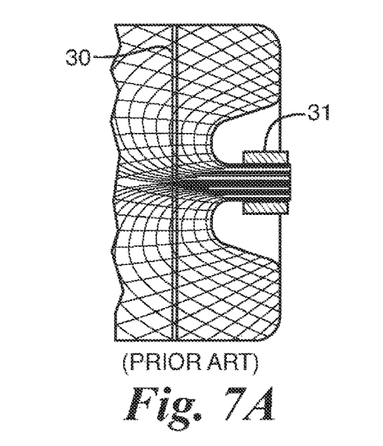
FIG. 7A shows a partial side cross-sectional view of a prior art occluder illustrating the clamp and clamp recess on one end of the device.
Figure 7B:
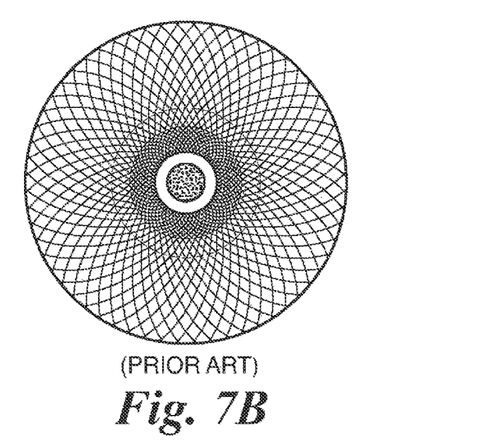
FIG. 7B shows a frontal end view of the occluder of FIG. 7A illustrating the clamp and clamp recess on one end of the device.

With reference to FIG. 7A, a partial side cross-sectional view and end view of a prior art occluder portion illustrating the clamp and clamp recess on one end of the device is shown. The device of FIG. 7A illustrates device designs whereby the surface containing the end clamp is recessed to make the device shorter. In FIG. 7A, a cross-sectional view is provided of a recessed end 30 and wire end clamp 31 of a prior art device.

Figure 7C:
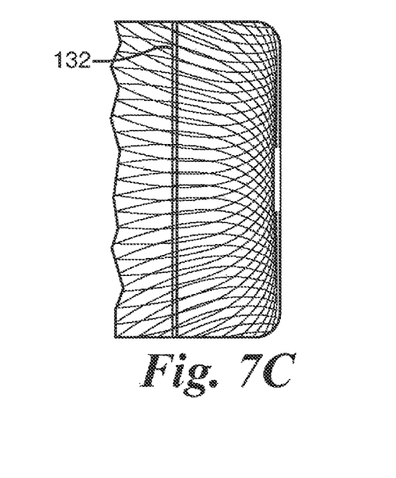
FIG. 7C shows a partial side cross-sectional of an occluder without end clamps in an embodiment of the present invention.
Figure 7D:
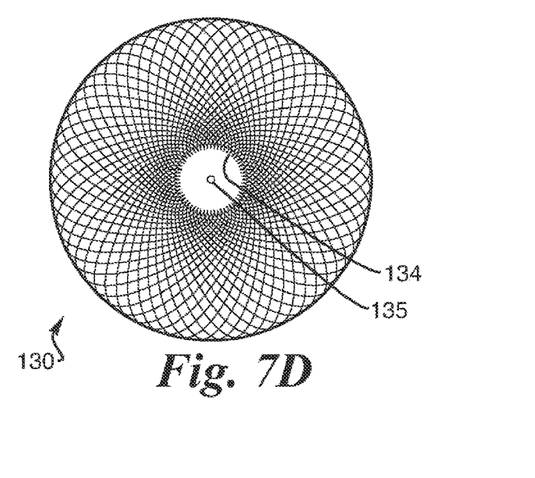
FIG. 7D shows a frontal end view of an occluder without end clamps in an embodiment of the present invention.

With reference to FIG. 7C, a partial side cross-sectional and end view of an occluder without end clamps in an embodiment of the present invention is shown. Recess 132 is eliminated in the design and wire ends 134 are cut after heat treatment such that wire ends 134 terminate near device central axis 135. Occluder 130 may have an optional polyester disc 112 or 114 sutured in for improved occlusion.

Figure 8A:
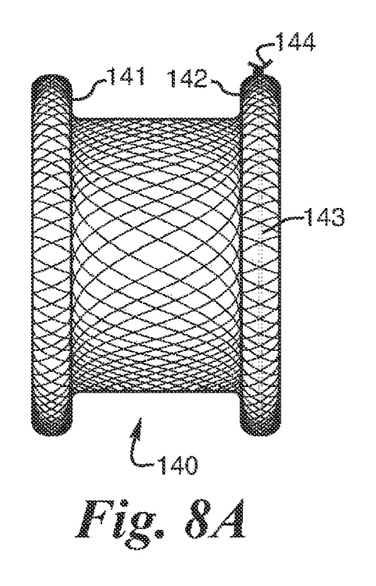
FIG. 8A shows a cross-sectional view of a design for either a flow restrictor or a shunt in an embodiment of the present invention.
Figure 8B:
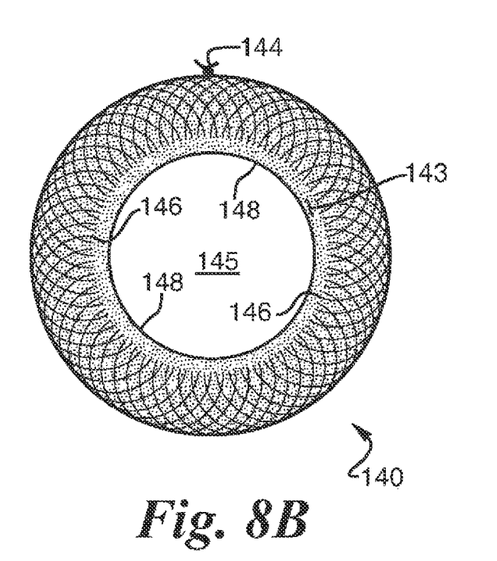
FIG. 8B shows a frontal end view of a design for either a flow restrictor or a shunt in an embodiment of the present invention.

With reference to FIG. 8, a side and end view respectively of a design for either a flow restrictor or a shunt in an embodiment of the present invention is shown. Braided device 140 has two raised flanges 141 and 142 which locate against the vessel surface to retain device 140. Flanges 141 and 142 are sized to be somewhat larger (e.g., 10-30%) than the vessel inside diameter to produce an outward force against the vessel wall to anchor device 140 and prevent dislodgement. An optional polyester fabric 143 is sutured 144 across raised flange 142 diameter. Fabric 143 has a hole 145 in the central portion, sized to create a flow limiting area as desired for the restriction of blood flow or shunting of blood through a vessel or across a membrane. In the case of shunting blood flow through a membrane raised flanges 141 and 142 would be more disc-like in shape and the discs would be separated by the thickness of the membrane with one disc on either side of the membrane and loaded against the membrane. In either design, the clamps in the prior art devices are replaced by un-bound cut wire ends 146 which are positioned to lie in device end surface 148. It is of note, that there are no clamps, recesses, or holes being forced through a braided fabric where the wires need to be manually rearranged and spaced evenly as in the prior art devices. This reduces manufacturing cost and provides a lower profile device that is easier to deliver.

Figure 9:
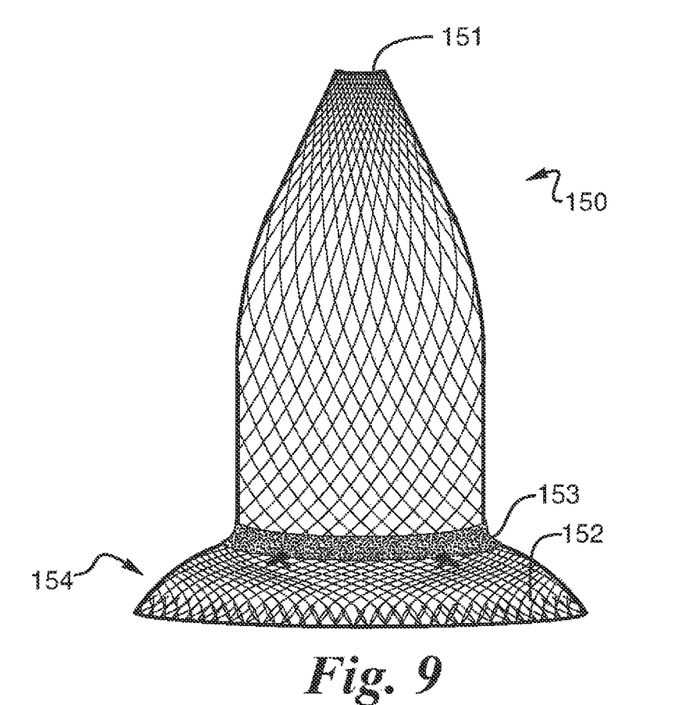
FIG. 9 shows a side view of another occluder embodiment of the present invention.

With reference to FIG. 9, a side view of another occluder embodiment of the present invention is shown. A PDA occluder is illustrated in a side view of bell shaped occluder 150. There are no clamps in device 150 and wire ends 151 are cut so as to be positioned near the central axis of the device's tapered distal end. Proximal device wire ends 152 are cut to length, such as to lie in a recessed surface within flange 154. Optionally, wire ends 152 could be cut to a longer length to end near the proximal device central axis. A polyester fabric 153 is optionally sutured across the diameter of the device distal flange 154 to improve thrombogenicity (reduce the time to occlusion).

Figure 10:
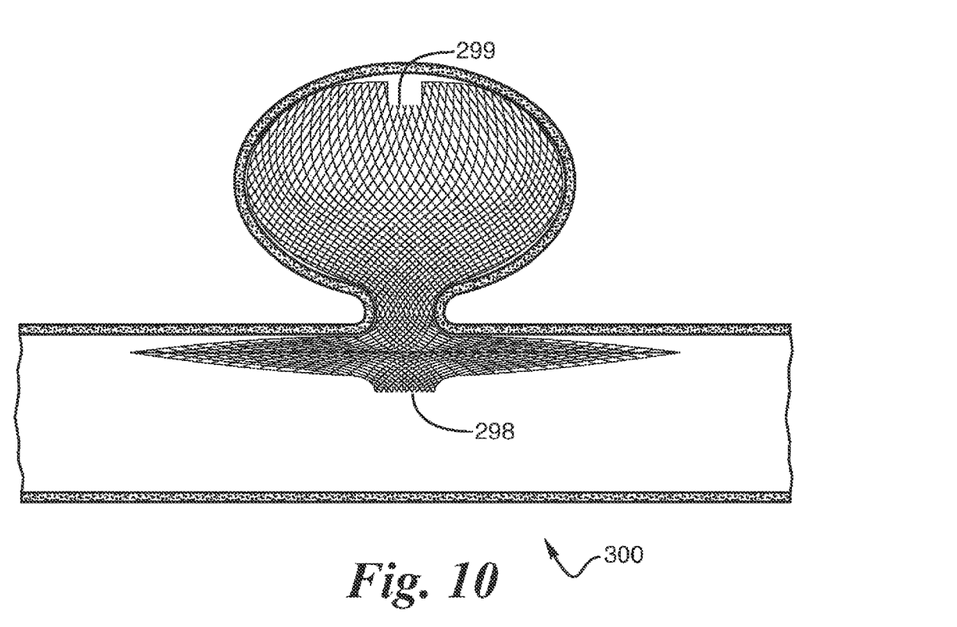
FIG. 10 shows a side view of an occluder shown occluding an aneurysm in an embodiment of the present invention.

With reference to FIG. 10, a side view of an occluder shown occluding an aneurysm in an embodiment of the present invention is illustrated. Occluder 300 could eliminate a distal recess and distal clamp and cut wire ends 299 to a length such that they are positioned near the distal axis of the device. The proximal clamp would be eliminated and proximal wire ends 298 cut to a length to position the ends in the flange outer surface facing the inside of the vessel. This improved design has minimal projection into the flow stream and thus the risk of a clot forming and breaking off from a clamp an entering the blood stream is diminished.

Further, it is anticipated that an occluder, stent, or flow restrictor could take any shape and could be offered for new applications or different anatomical conditions. In addition it is contemplated that a device may be fabricated using multiple metal fabric layers. The individual layer wire ends could be cut to the same length or have staggered cut ends. The multiple layers could increase the metal content of the device and cause quicker occluding times, thus eliminating the need for polyester or other fabric to improve throbogenicity. The multiple layers could be sutured together in a central area and generally at least one layer could be a primary structural layer while one or more layers could be of lesser radial strength and generally of smaller wire diameter and smaller pore size between filaments. The braided pitch of each layer could generally be the same to allow uniform expansion and contraction. The layers may have the same or different shapes to fill a hollow space within the outer layer. A multi-layered device may in addition include an occluding fiber within the hollow portion of the device or one or more layers may be coated with a drug to promote clotting or if desired with a drug such as heparin to inhibit thrombus formation, depending on the application.

Those skilled in the art will appreciate that in order to speed up the occlusion of the vessel; the device may be coated with a suitable thrombogenic agent, filled with a polyester fiber or braided with an increased number of wire strands. This fiber easily collapses with the device for delivery through a catheter. This fiber is also useful for occlusion devices, although use of multiple-layers of braided fabric may function in a similar manner to the polyester fabric to speed thrombosis. The interwoven fiber by attachment to clot retains the clot firmly within the device as it forms the occlusion.

The tubular braid used to fabricate occlusion devices for example, in embodiments of the present invention may range from wire having a diameter of 0.002 to 0.005 inch, possibly in the range of 0.003 to 0.0035 inch and for a PDA device possibly 0.003 inch diameter. The number of wires in the tubular braid may vary from 36 to 144 but it is most helpful if it is in the range of 72 to 144 and for a PDA device is preferably 144 wires. The pick count of the braid may vary from 30 to 100 and preferably from 50 to 80 and for a PDA device is preferably 70.

Figure 11:
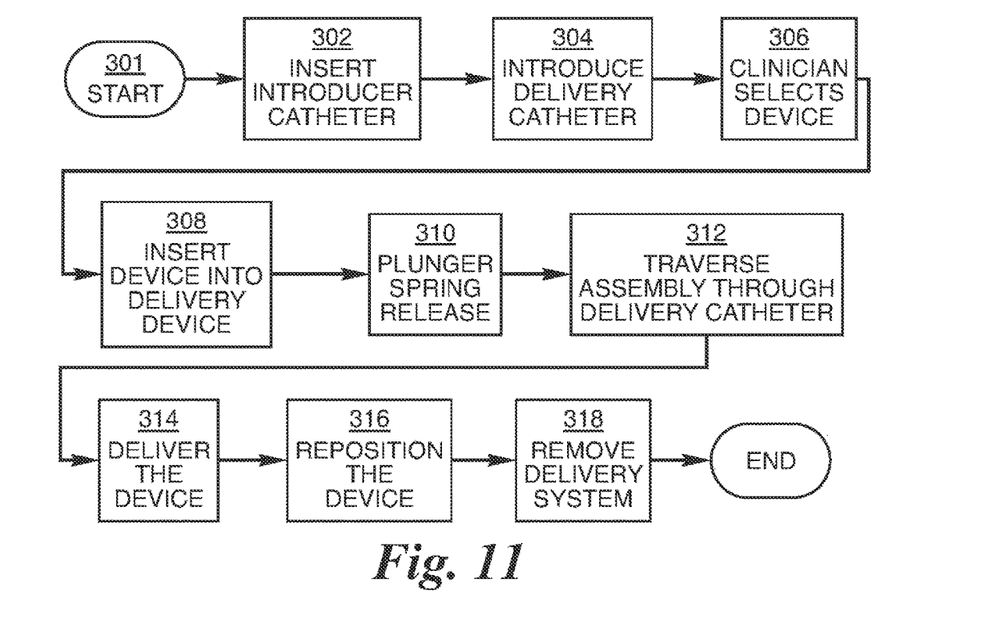
FIG. 11 shows a flow chart diagram of a method of implantation of a medical device in accordance with embodiments of the present invention.

With reference to FIG. 11, a flow chart diagram of a method of implantation of a medical device in accordance with embodiments of the present invention is shown. A part of a method of implantation 301, once access has been obtained to a vessel, an introducer catheter is inserted into the vessel and maintains a position from outside the body to within a vessel such as the femoral artery at state 302. Access to the patient's vessel of treatment is obtained using the Seldinger Technique as is commonly known in the art. Delivery catheter 124 can be placed into vasculature and navigated to the treatment site such that the distal end of catheter 124 is adjacent the treatment site at state 304. A clinician could select a medical device suitable for the condition being treated at state 306. The device could be furnished separately or could be pre-loaded onto a delivery device as is illustrated in FIG. 5D. If furnished separately, a device could be in a reduced diameter sleeve with the proximal device wire ends exposed for loading into the delivery device. A delivery catheter could be selected based on the particular device and anatomical conditions. The delivery device could be first placed through the lumen of the delivery catheter until the distal end is adjacent the distal end of the catheter at step 308.

With reference again to FIG. 5D, occluder 100 having proximal wire ends 106 and 108 could be inserted over plunger 123 into delivery device sleeve 120 at state 308 while the spring loaded frusto-conical plunger 123 is advanced distally with respect to sleeve 120 to open sleeve access 126. Once wire ends 106 or 108 are inserted into sleeve 120, plunger spring 123 can be released to move plunger 123 proximally toward wire ends 106 or 108 at state 310. Spring pressure locks wire ends 106 or 108 between sleeve 120 and the plunger surface. Delivery device 121 and occluder 100 may now be drawn together proximally to draw occluder 100 into lumen 127 of delivery catheter 124 adjacent the distal end at state 312. Since occluder 100 can be formed from Nitinol and can have shape memory, this reduction in diameter does not harm occluder 100.

Delivery catheter 124 can be slowly pulled proximal while holding back on delivery device 121 to allow the distal end of occluder 100 to emerge from delivery catheter 124 and to self expand to its pre-determined shape at state 314. If occluder 100 is not positioned as desired occluder 100 may be returned to delivery catheter 124 by either advancement of delivery device 121 while holding delivery catheter 124 stationary or holding delivery catheter stationary 124 and pulling proximally on delivery device 121 at state 316. In the case of flanged or double disk devices where one disk is placed on either side of a septum, delivery catheter 124 distal end is placed distal to the septum and then withdrawn partially relative to the delivery device 121 to allow the distal disk only to self expand. The delivery catheter 124 and delivery device 121 are now pulled proximally together to locate the first expanded disk against the septum. The delivery catheter 124 is now withdrawn proximally while holding the delivery device 121 in place to allow the second disk to self expand on the proximal side of the septum. Assuming occluder 100 is positioned as desired, fully deployed plunger 123 may be displaced distally relative to sleeve 120 to release occluder 100. Delivery catheter 124 and delivery device 121 can next be removed from the body leaving occluder 100 implanted in the vessel, cavity, or treatment site at state 318.

In an alternative method of treatment delivery catheter 124 may first be placed into the desired treatment site using a technique of advancement over a steerable guide wire as well know in the interventional medical art. Occluder 100 may be connected to delivery device 121 as previously stated and occluder 100 and delivery device 121 advanced into the proximal end of delivery catheter 124 using a tear-away introducer tapered to pilot into delivery catheter 124 and coaxially placed over the delivery device 121 distal end. Once occluder 100 is within catheter 124 the tear-away introducer is removed and occluder 100 advanced adjacent the distal end of delivery catheter 124. In all other aspects, occluder 100 placement is as previously described. Delivery catheter 124 may be a guide catheter or steerable sheath in other embodiments.

In another embodiment of the delivery device disclosed in patent application US 2007/0118207A1, the delivery system 129 replaces wire or cable 122 (FIG. 5D) with a hollow tube suitable for passage of a guidewire there through. In such cases where the guide catheter 124 is introduced into the vasculature over a guidewire prior to device selection, the delivery catheter may be advanced over the guidewire within the guide catheter. In all other aspects the procedure is similar.

Thus, embodiments of the BRAIDED VASCULAR DEVICES HAVING NO END CLAMPS are disclosed. One skilled in the art will appreciate that the present teachings can be practiced with embodiments other than those disclosed. The disclosed embodiments are presented for purposes of illustration and not limitation, and the present teachings are limited only by the claims that follow.

What is claimed is:

1. A medical device, comprising:
a plurality of metal strands woven into a tubular metal fabric having a longitudinal axis, a proximal end, a distal end, and a segment therebetween, the tubular metal fabric having wire ends at each of the proximal and distal ends and an expanded preset configuration, the expanded preset configuration being deformable to a lesser cross-sectional dimension for delivery through a channel in a patient's body, the tubular metal fabric having a memory property whereby the tubular metal fabric returns to the expanded preset configuration, the wire ends being unsecured and free at each of the proximal and distal ends such that the wire ends are exposed, wherein the free wire ends at each of the proximal and distal ends extend radially inward with respect to the longitudinal axis to an opening having an inner diameter smaller than an outer diameter of at least a portion of the segment, and further wherein the free wire ends of at least one of the proximal and distal ends of the tubular metal fabric define an end wall arranged within a plane perpendicular to the longitudinal axis such that the free wire ends of the at least one of the proximal and distal ends are positioned in the plane of the end wall.

2. The medical device of claim 1, wherein the tubular metal fabric is selected from the group consisting of an occluder, a shunt, and a flow restrictor.

3. The medical device of claim 1, further comprising:
an occluding fiber retained within an expandable hollow central portion formed by the tubular metal fabric.

4. The medical device of claim 1, wherein the tubular metal fabric is manufactured from an alloy selected from the group consisting of stainless steel, nickel-titanium, and cobalt-chromium-nickel.

5. The medical device of claim 1, wherein at least a portion of the segment of the tubular metal fabric is in the shape of a disc in the expanded preset configuration.

6. The medical device of claim 1, wherein the tubular metal fabric is in the shape of a dumbbell in the expanded preset configuration with two expanded diameter portions separated by a reduced diameter portion formed between the proximal and distal ends.

7. The medical device of claim 6, wherein the free wire ends are heat-treated to prevent unraveling.

8. The medical device of claim 6, wherein the tubular metal fabric is adapted for delivery to a treatment site in a patient with a clamping force against an inner lumen of a delivery device.

9. The medical device of claim 6, wherein the free wire ends are co-planar with a respective plane defined by the expanded diameter portions of each of the proximal and distal ends.

10. The medical device of claim 6, further comprising:
a thrombogenic agent located on the tubular metal fabric.

11. The medical device of claim 1, wherein at least a portion of the segment of the tubular metal fabric comprises two discs, wherein one of the two discs is adjacent the proximal or distal end in the expanded preset configuration.

12. The medical device of claim 11, wherein each of the two discs is adjacent the proximal and distal ends of the tubular metal fabric, respectively.

13. The medical device of claim 1, wherein the segment comprises a flow passage therethrough.

14. The medical device of claim 1, further comprising:
a polyester fabric attached to the tubular metal fabric.

15. The medical device of claim 1, wherein the tubular metal fabric is adapted for delivery to a treatment site in a patient with a clamping force against an inner lumen of a delivery device.

16. The medical device of claim 1, wherein the tubular metal fabric is formed from a shape memory alloy.

17. The medical device of claim 16, wherein the shape memory alloy is Nitinol.

18. A medical device, comprising:
a tubular braided metal fabric having a proximal end, a distal end, and a longitudinal axis extending therebetween, the tubular braided metal fabric comprising:
a plurality of metal strands woven to define the tubular braided metal fabric and having wire ends at each of the proximal and distal ends, the plurality of metal strands formed of a memory material and shaped such that the tubular braided metal fabric has an expanded preset configuration;
an expanded diameter portion at the proximal or distal end in the expanded preset configuration; and
a reduced diameter portion disposed between the proximal and distal ends and having a smaller outer diameter than the expanded diameter portion in the expanded preset configuration,
wherein the wire ends are unsecured and free at each of the proximal and distal ends such that the wire ends are exposed,
wherein the free wire ends at each of the proximal and distal ends extend radially inward with respect to the longitudinal axis and along respective planes to define an end wall at each of the proximal and distal ends,
and wherein the end wall defined by at least one of the proximal and distal ends of the tubular metal fabric is arranged within a plane perpendicular to the longitudinal axis.

* * * * *